United States Patent
Le Neel et al.

(10) Patent No.: US 10,905,362 B2
(45) Date of Patent: Feb. 2, 2021

(54) FLEXIBLE ELECTROCHEMICAL MICRO-SENSOR

(71) Applicant: STMICROELECTRONICS PTE LTD, Singapore (SG)

(72) Inventors: Olivier Le Neel, Saint-Martin-d'Uriage (FR); Suman Cherian, Kerala (IN); Calvin Leung, Singapore (SG)

(73) Assignee: STMICROELECTRONICS PTE. LTD., Singapore (SG)

(*) Notice: Subject to any disclaimer, the term of this patent is extended or adjusted under 35 U.S.C. 154(b) by 0 days.

(21) Appl. No.: 16/407,054

(22) Filed: May 8, 2019

(65) Prior Publication Data

US 2019/0261899 A1 Aug. 29, 2019

Related U.S. Application Data

(63) Continuation of application No. 15/873,557, filed on Jan. 17, 2018, now Pat. No. 10,299,711, which is a continuation of application No. 14/200,828, filed on Mar. 7, 2014, now Pat. No. 9,918,667.

(51) Int. Cl.
*G01N 27/327* (2006.01)
*A61B 5/1473* (2006.01)
*A61B 5/145* (2006.01)
*A61B 5/1468* (2006.01)

(52) U.S. Cl.
CPC .......... *A61B 5/1473* (2013.01); *A61B 5/1468* (2013.01); *A61B 5/14532* (2013.01); *G01N 27/3272* (2013.01)

(58) Field of Classification Search
CPC . A61B 5/1473; A61B 5/1468; A61B 5/14532; G01N 27/3272
See application file for complete search history.

(56) References Cited

U.S. PATENT DOCUMENTS

| | | | |
|---|---|---|---|
| 4,951,122 A | 8/1990 | Tsubosaki et al. | |
| 7,144,486 B1 | 12/2006 | Fritsch et al. | |
| 8,860,152 B2 | 10/2014 | Cherian et al. | |
| 8,917,812 B2 | 12/2014 | Ikhlef | |
| 2003/0146110 A1* | 8/2003 | Karinka | C12Q 1/002 205/777.5 |
| 2005/0272989 A1 | 12/2005 | Shah et al. | |

(Continued)

*Primary Examiner* — J. Christopher Ball
(74) *Attorney, Agent, or Firm* — Seed IP Law Group LLP

(57) ABSTRACT

A universal electrochemical micro-sensor can be used either as a biosensor or an environmental sensor. Because of its small size and flexibility, the micro-sensor is suitable for continuous use to monitor fluids within a live subject, or as an environmental monitor. The micro-sensor can be formed on a reusable glass carrier substrate. A flexible polymer backing, together with a set of electrodes, forms a reservoir that contains an electrolytic fluid chemical reagent. During fabrication, the glass carrier substrate protects the fluid chemical reagent from degradation. A conductive micromesh further contains the reagent while allowing partial exposure to the ambient biological or atmospheric environment. The micromesh density can be altered to accommodate fluid reagents having different viscosities. Flexibility is achieved by attaching a thick polymer tape and peeling away the micro-sensor from the glass carrier substrate. The final structure is thereby transferred to the polymer tape, providing a flexible product.

20 Claims, 9 Drawing Sheets

(56) References Cited

U.S. PATENT DOCUMENTS

2012/0168882 A1* 7/2012 Cherian .......... G01N 33/48785
257/414
2013/0334579 A1 12/2013 Accardi et al.
2014/0291677 A1 10/2014 Le Neel et al.

* cited by examiner

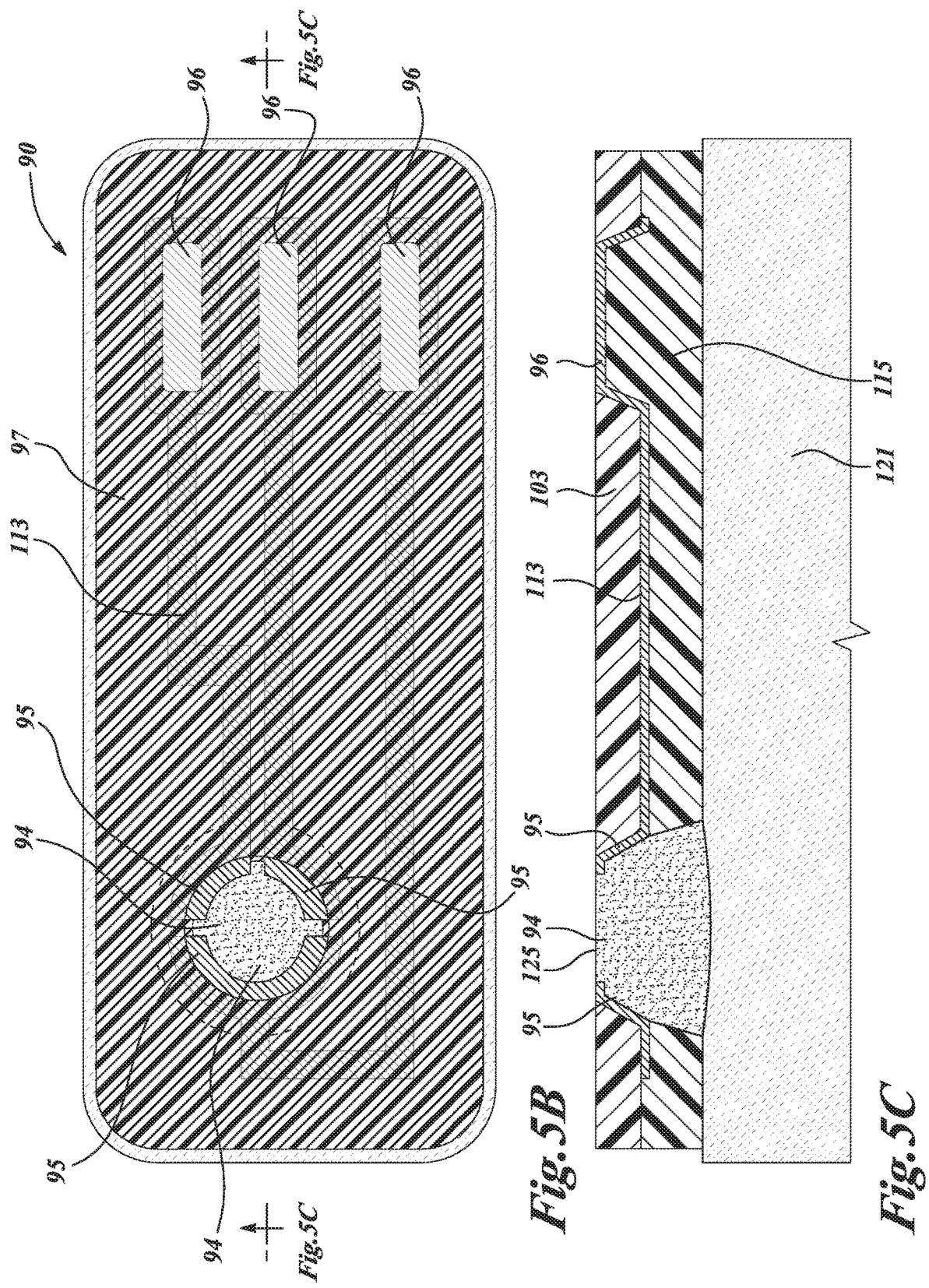

FLEXIBLE ELECTROCHEMICAL MICRO-SENSOR

BACKGROUND

Technical Field

The present disclosure generally relates to microelectronic sensors, and in particular, to consumable biosensors that are flexible and can contain a fluid for electrochemical monitoring.

Description of the Related Art

Biosensor strips are used to monitor blood glucose levels by millions of patients who suffer from diabetes. With reference to FIG. 1, a typical home monitoring apparatus 80 includes a conventional disposable strip biosensor 82 and a portable electronic monitor 83. A blood sample is applied to the biosensor 82, and the strip is inserted into the portable electronic monitor 83. A conventional biosensor 82 is made of a semi-rigid backing material 84 approximately an inch long, impregnated with an electrolytic chemical reagent 86 at one end and printed with electrodes 88 at the other end. The patient pricks a fingertip, applies a drop of blood 89 to the reagent 86, and inserts the electrodes 88 into the portable electronic monitor 83. The electrolytic chemical reagent 86 conducts a current that is proportional to an amount of glucose in the blood. Current flow conducted via the electrodes 88 in the biosensor 82 closes a circuit when the biosensor 82 is inserted into the portable electronic monitor 83. The current in the circuit can then be measured by the portable electronic monitor 83. The portable electronic monitor 83 is configured with software that converts the current measurement into a numerical value that represents the blood glucose level. The portable electronic monitor 83 then provides a digital readout of the numerical value and stores the numerical value as blood glucose data in an electronic memory. By either recording or downloading the blood glucose data, the patient can track blood glucose values over time to adjust insulin dosage.

A drawback for manufacturers is that the chemical reagent, which is typically in liquid form, must be cross-linked into a solid form that is suitable for incorporation into the biosensor strip. Furthermore, techniques used to fabricate the electrodes, the chemical reagent, and the packaging are specific to three different industries, namely the semiconductor, bio-chemistry, and packaging industries, respectively. Thus, the current sensors and manufacturing process tend to be costly, overly complex, and disjointed, which results in a higher product cost to consumers.

In-situ monitoring systems offer many advantages over the patient-administered home monitoring system described above. In one type of in-situ monitoring system, a transdermal patch is used to secure a blood sampling needle and a drug delivery needle to a patient's skin. Blood glucose can be detected by a circuit within the patch, and the data can be wirelessly relayed by an antenna in the patch for remote processing and dose calculation. Likewise, a wireless signal containing the determined dosage information can be received by an antenna in the patch and used to electronically control insulin delivery. By automating the monitoring and dosing functions, such a system eliminates the need for patients to handle fluid chemical reagent strips or syringes of insulin. However, although the transdermal patch is generally more accurate and more convenient than the home monitoring system, it is still cumbersome. For example, the patient must apply the transdermal patch, wear the patch at all times, and periodically re-load the patch with insulin. Because it is not fully automated, the transdermal patch still incurs opportunities for error in dosing.

There also exist environmental micro-sensors, such as temperature and humidity sensors, that monitor environmental conditions by exposing dielectric films that are sensitive to ambient conditions. Embodiments of such sensors are described in U.S. patent application Ser. Nos. 13/853,732 and 13/315,477, for example. Some environmental sensors are integrated with chemical sensors, as disclosed in U.S. Patent Application Publication No. US 2012/0168882. However, existing micro-sensors are typically tailored for either a bio-medical or an environmental application, and are generally not interchangeable.

BRIEF SUMMARY

A universal electrochemical fluid micro-sensor, as described herein, can be used either as a biosensor or as an environmental sensor. Because of its small size and flexibility, the universal fluid electrochemical micro-sensor is suitable for continuous use as, for example, an in-situ micro-sensor device disposed within a human or animal subject, or in an amperometric or potentiometric environmental measurement device. When used as a biosensor, the device can be configured with different fluid electrochemical reagents to monitor blood glucose, blood-borne viruses such as HIV, cardiac marker enzymes, heart attack residue chemicals, and the like. When used as an environmental sensor, the device can be configured with different fluid electrochemical reagents to measure ambient temperature, humidity, barometric pressure, oxygen concentration, and the like. Such a fluid micro-sensor can be disposable, intended for one-time use, or semi-disposable, having a one-month operational lifetime.

BRIEF DESCRIPTION OF THE SEVERAL VIEWS OF THE DRAWINGS

In the drawings, identical reference numbers identify similar elements. The sizes and relative positions of elements in the drawings are not necessarily drawn to scale.

FIG. 5B is a top plan view of the completed micro-sensor following separation from a glass carrier substrate. In FIG. 5B, the micro-sensor is inverted with respect to the illustration shown in FIG. 4D.

FIG. 5C is a cross-sectional view of the completed micro-sensor shown in FIG. 5B.

DETAILED DESCRIPTION

Figure 1:
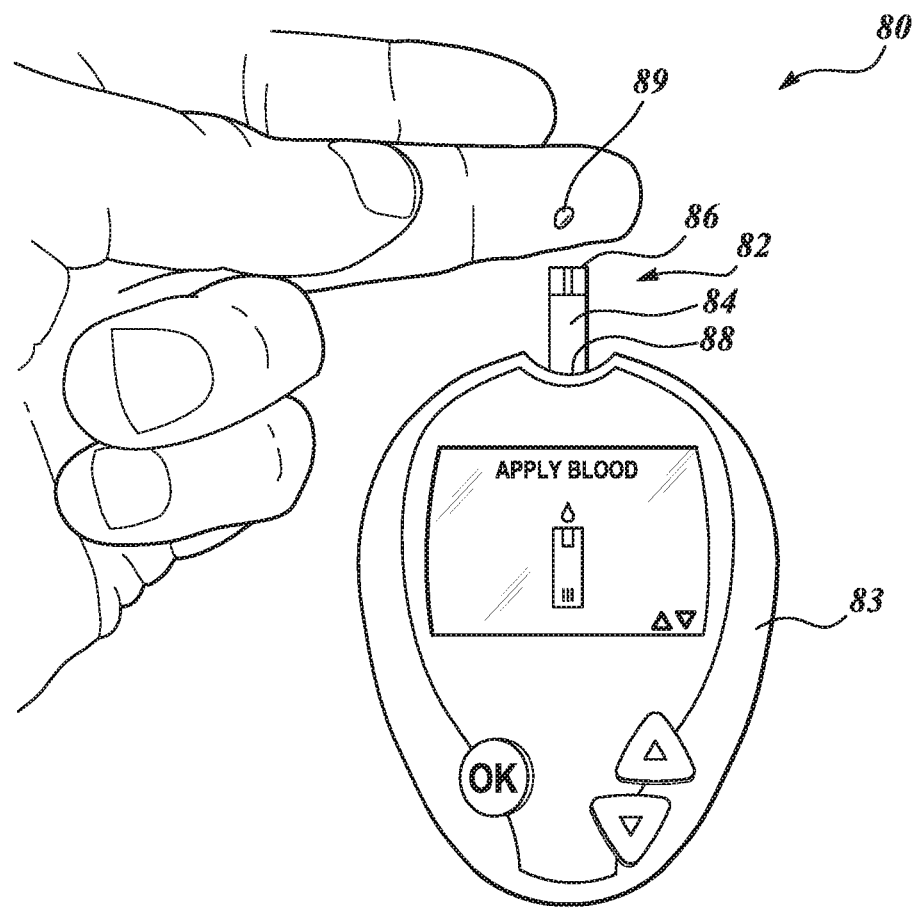
FIG. 1 shows use of an existing blood glucose monitoring system.

In the following description, certain specific details are set forth in order to provide a thorough understanding of various aspects of the disclosed subject matter. However, the disclosed subject matter may be practiced without these specific details. In some instances, well-known structures and methods of semiconductor processing comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising" are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to integrated circuits is generally intended to include integrated circuit components built on semiconducting substrates, whether or not the components are coupled together into a circuit or able to be interconnected. Throughout the specification, the term "layer" is used in its broadest sense to include a thin film, a cap, or the like, and one layer may be composed of multiple sub-layers.

Reference throughout the specification to conventional thin film deposition techniques for depositing silicon nitride, silicon dioxide, metals, or similar materials includes such processes as chemical vapor deposition (CVD), low-pressure chemical vapor deposition (LPCVD), metal organic chemical vapor deposition (MOCVD), plasma-enhanced chemical vapor deposition (PECVD), plasma vapor deposition (PVD), atomic layer deposition (ALD), molecular beam epitaxy (MBE), electroplating, electro-less plating, and the like. Specific embodiments are described herein with reference to examples of such processes. However, the present disclosure and the reference to certain deposition techniques should not be limited to those described. For example, in some circumstances, a description that references CVD may alternatively be done using PVD, or a description that specifies electroplating may alternatively be accomplished using electro-less plating. Furthermore, reference to conventional techniques of thin film formation may include growing a film in-situ. For example, in some embodiments, controlled growth of an oxide to a desired thickness can be achieved by exposing a silicon surface to oxygen gas or to moisture in a heated chamber.

Reference throughout the specification to conventional photolithography techniques, known in the art of semiconductor fabrication for patterning various thin films, includes a spin-expose-develop process sequence typically followed by an etch process. Alternatively or additionally, photoresist can also be used to pattern a hard mask (e.g., a silicon nitride hard mask), which, in turn, can be used to pattern an underlying film.

Reference throughout the specification to conventional etching techniques known in the art of semiconductor fabrication for selective removal of polysilicon, silicon nitride, silicon dioxide, metals, photoresist, polyimide, or similar materials includes such processes as wet chemical etching, reactive ion (plasma) etching (RIE), washing, wet cleaning, pre-cleaning, spray cleaning, chemical-mechanical planarization (CMP) and the like. Specific embodiments are described herein with reference to examples of such processes. However, the present disclosure and the reference to certain deposition techniques should not be limited to those described. In some instances, two such techniques may be interchangeable. For example, stripping photoresist may entail immersing a sample in a wet chemical bath or, alternatively, spraying wet chemicals directly onto the sample.

Specific embodiments are described herein with reference to electrochemical micro-sensors that have been produced; however, the present disclosure and the reference to certain materials, dimensions, and the details and ordering of processing steps are exemplary and should not be limited to those shown.

Figure 2:
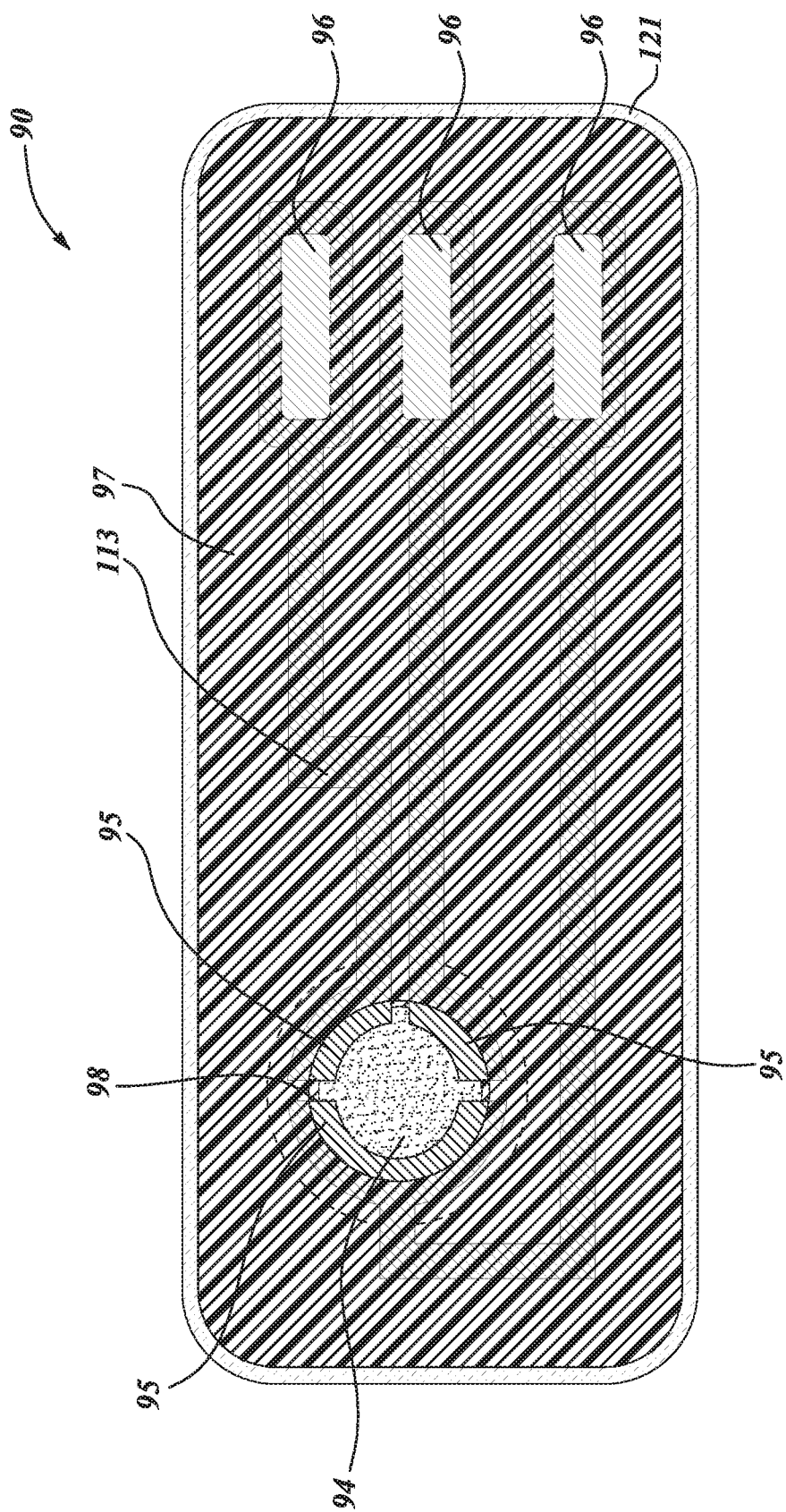
FIG. 2 is a top plan view of a universal electrochemical fluid micro-sensor, according to one embodiment described herein.

FIG. 2 shows an exemplary embodiment of a universal fluid electrochemical micro-sensor 90 that includes a volume of a fluid chemical reagent 94 at one end, and electrodes 95 in contact with the fluid chemical reagent 94. Electrical signals are accessible via contacts 96 coupled to the electrodes 95 by traces 113. Unlike the conventional biosensor 82, the universal fluid electrochemical micro-sensor 90 is formed on a flexible backing 97 that can incorporate one or more polymer films. Furthermore, the fluid electrolytic chemical reagent 94 need not be impregnated into the flexible backing 97. Instead, the polymer films and the electrodes together form a reservoir 98 that contains the fluid chemical reagent 94. A tape 121 on the back side can provide additional support.

In one embodiment, the electrodes 95 contact the fluid chemical reagent 94 along a perimeter of the reservoir 98. In another embodiment, an optional species inlet net, in the form of a conductive micromesh, covers the surface of the fluid chemical reagent 94 to keep it contained while allowing exposure of a portion of the surface area of the fluid chemical reagent 94 to the ambient biological or atmospheric environment; see, for example, FIGS. 6B and 6C. The conductive micromesh can be electrically coupled to one or more of the electrodes 95 either by a wired connection, or by capacitive coupling. The density of the conductive micromesh can be altered to accommodate fluid reagents having different viscosities. For example, a fluid reagent in the form of a gel can be held in place with a wider micromesh than a fluid reagent in the form of a less viscous liquid. Through use of the conductive micromesh, it is not necessary to cross-link the fluid chemical reagent 94 to prevent the fluid from flowing out of the device.

The micro-sensors disclosed have a greater degree of flexibility than conventional semi-rigid sensors. Such flexibility is achieved by a special fabrication process in which a micro-sensor is built on a glass carrier substrate, and is then removed from the carrier substrate by attaching a thick polymer tape and peeling away the micro-sensor from the glass carrier substrate. The final structure is thereby transferred to the polymer tape, which is very flexible. The glass carrier substrate can then be re-used.

Figure 3:
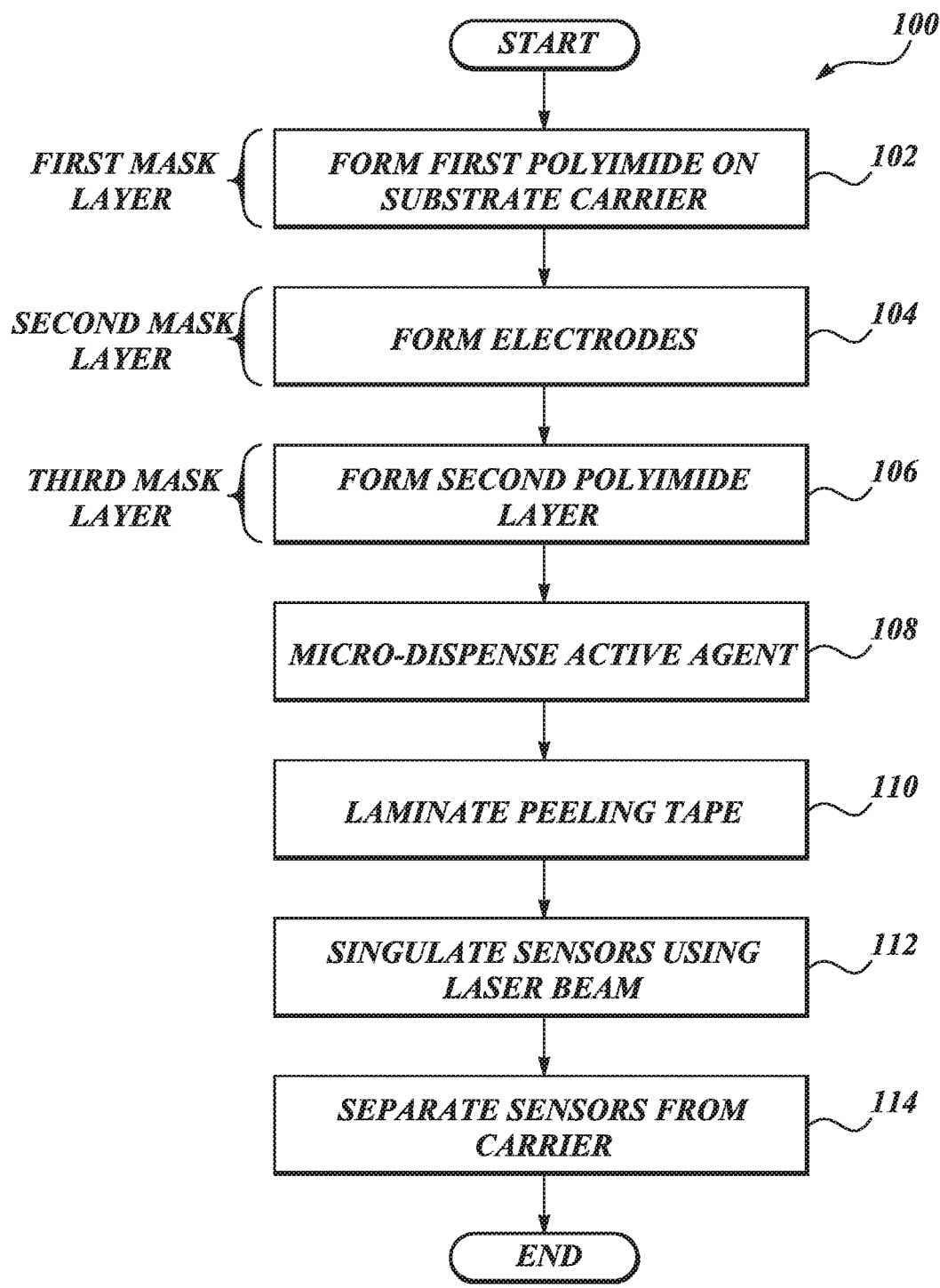
FIG. 3 is a flow diagram showing steps in a method of making the universal electrochemical fluid micro-sensor shown in FIG. 2.

With reference to FIGS. 3-5D, fabrication of one embodiment of the universal fluid electrochemical micro-sensor 90, according to an exemplary method 100, is shown and described. FIG. 3 shows a high level sequence of steps in the exemplary method 100. FIGS. 4A-5D illustrate formation of the universal fluid electrochemical micro-sensor having a single reservoir 98, step-by-step, following the method 100. The method 100 is efficient in that it entails only three mask layers, one micro-dispense step, and one laser cutting step. The method 100 allows for a continuous, integrated process flow in which the electrodes, chemical reagent, and packaging are easily assembled.

The universal fluid electrochemical micro-sensor 90 can be used as a biosensor, for example, as an in-situ continuous blood glucose monitor, or as an environmental sensor immersed in an atmospheric or aqueous environment. The exemplary method 100 produces flexible electrochemical micro-sensors using only three mask layers. According to the method 100, the flexible electrochemical micro-sensors are constructed upside down and inverted at the end so that the first layer formed is the top of the universal fluid electrochemical micro-sensor 90 and the last layer formed is the bottom of the micro-sensor.

Figure 4A:
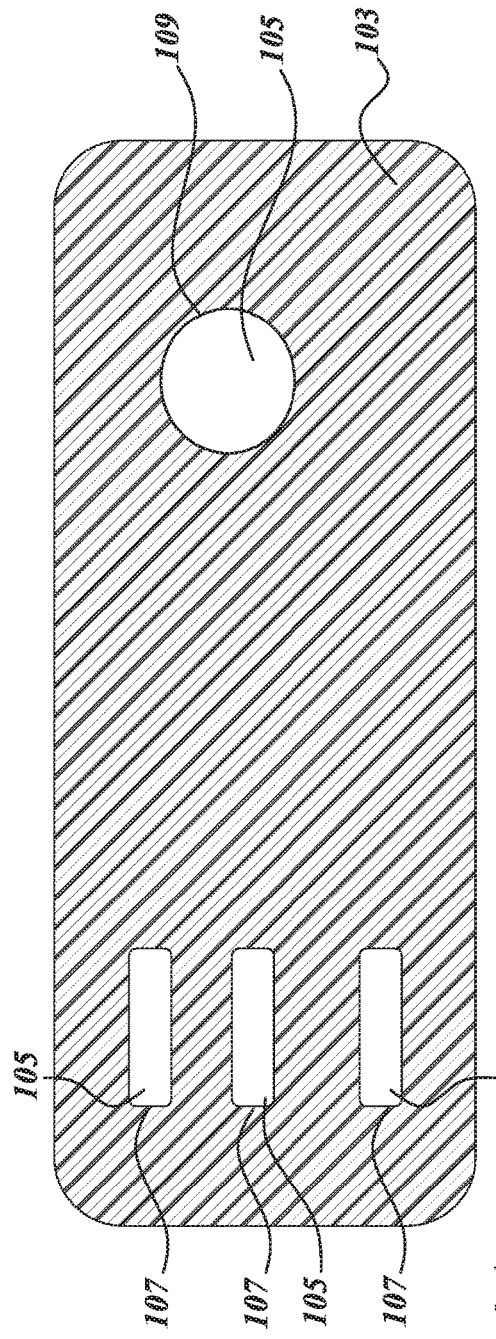
FIGS. 4A-4C are top plan views of the partially made universal electrochemical fluid micro-sensor after carrying out various steps in the method shown in FIG. 3.

At 102, a first polymer layer 103 is deposited on a rigid substrate 105. Contact holes 107 and a first well opening 109 are formed in the first polymer layer 103. If the first polymer layer 103 is a photosensitive polymer such as polyimide, patterning the contact holes 107 and the well opening 109 can be accomplished by exposing the first polymer layer 103 through a mask and rinsing away either the exposed or non-exposed portions, depending on whether the photosensitive polymer is positive or negative. FIG. 4A shows one embodiment of a partially fabricated electrochemical micro-sensor after the first polymer layer 103 has been formed and patterned with the contact holes 107. The underlying rigid substrate 105 shows through the contact holes 107. In one embodiment, the rigid substrate 105 is a 500-600 µm thick glass carrier that is used as a support during formation of the micro-sensors. The rigid substrate 105 is desirably made in the form of a disc so it can be processed in substantially the same fashion as a semiconductor wafer, but at a much lower cost because glass substrates are much less expensive than silicon substrates.

In one embodiment, the first and second polymer layers, 103 and 115, respectively, which form the flexible backing 97, are made of polyimide, although other polymers could be used instead. As a photosensitive material, polyimide can be spun on to a thickness within the range of about 4-10 µm, exposed to light through a mask, and portions can be removed by a chemical developer using a standard lithography process, as is well known in the art. Three patterned contact holes 107 are shown at the left end of the first polymer layer 103, and a circular well opening 109 is shown at the right end of the first polymer layer 103. Following patterning, the first polymer layer 103 is cured, for example, by exposure to ultraviolet light in a chamber that is heated to a temperature of about 100-300 C.

Figure 4B:
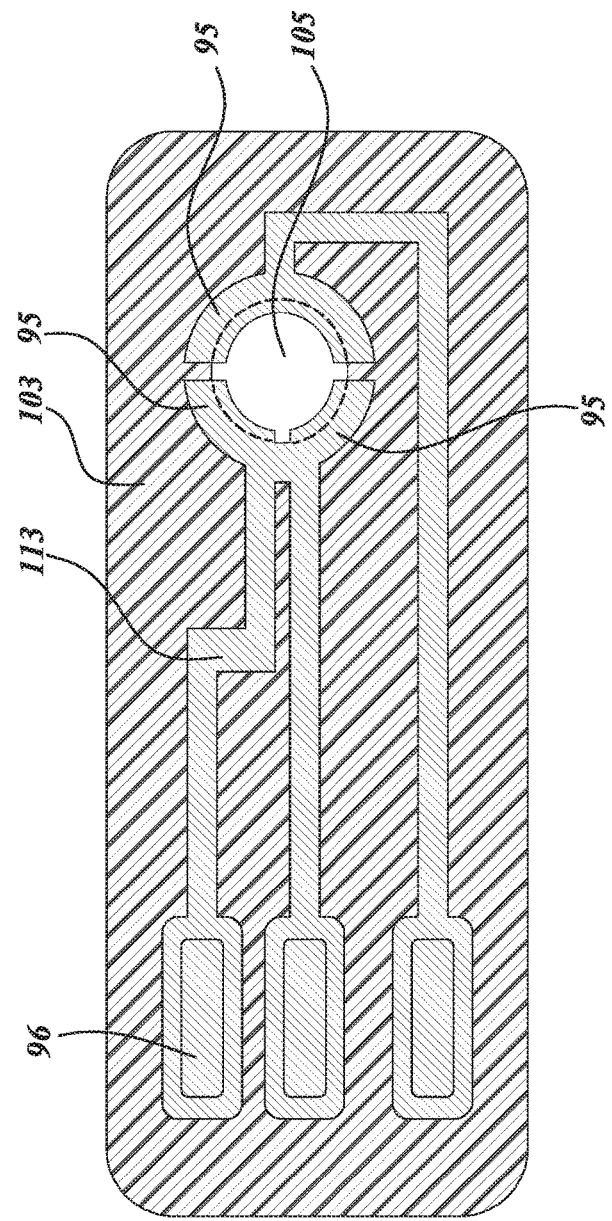

At 104, the electrodes 95 are formed around a perimeter of the well opening 109, and contacts 96 are formed over the contact holes 107, using a second mask. The electrodes 95 are coupled to the contacts 96 by traces 113. FIG. 4B shows one embodiment of a partially fabricated fluid electrochemical micro-sensor following formation of the contacts 96, electrodes 95, and traces 113. The electrodes 95 and traces 113 are desirably made of gold, or another biocompatible conducting material such as platinum or carbon. The contacts 96 are designed to plug into a device such as the electronic blood glucose monitor described above. Additionally or alternatively, the electrodes 95 can operate as antennas, similar to RFID tags, wherein the electrodes 95 can communicate data wirelessly to a database or server located at, for example, a physician's office, a hospital, or a weather station. A gold film can be deposited and patterned using, for example, a plasma vapor deposition process, and a wet chemical etching process or a reactive ion etch process so as to form the electrodes 95 and traces 113 together in the same mask layer. Each one of the rectangular contacts 96 overlaps a contact hole 107 and is coupled, via a separate trace 113, to a corresponding electrode 95 in the form of an arc segment. Each arc segment overlaps a portion of the perimeter of the circular well opening 109, partially surrounding the fluid chemical reagent 94. The arc segments are spaced apart by gaps to ensure they are electrically isolated from one another. Three arc segments are shown, of which one is a reference electrode, and one is a work function electrode.

Figure 4C:
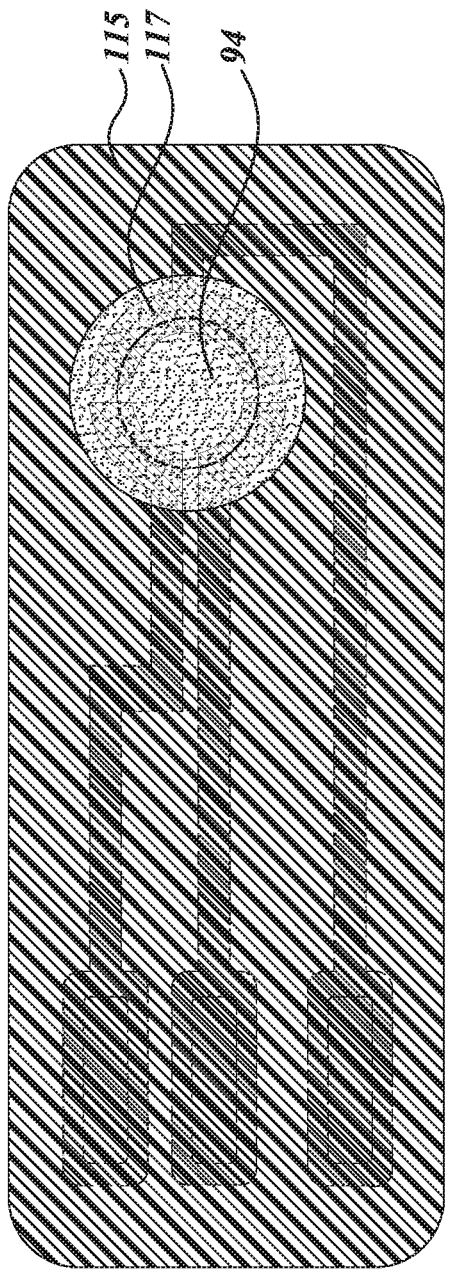

At 106, a second polymer layer 115 is deposited, and a second well opening 117 is formed in the second polymer layer 115. Patterning the second polymer layer 115 makes use of a third mask. FIG. 4C shows one embodiment of the partially fabricated fluid electrochemical micro-sensor following formation of the second polymer layer 115 and dispensing of the fluid chemical reagent 94 to form an active layer. The second polymer layer 115 is spun on top of the electrodes 95, and is patterned, in similar fashion to the first polymer layer 103, with a second well opening 117 that coincides with the first well opening 109. Following patterning, the second polymer layer 115 is cured, for example, by exposure to ultraviolet light in a chamber that is heated to a temperature below 400 C, for example, within the range of about 100-300 C. Thus is formed a well suitable for containing a fluid. The bottom of the well is formed by the substrate 105. The sides of the well are formed by a combination of the first and second polymer layers 103 and 115, together with and the electrodes 95, that are at least partially embedded therebetween.

At 108, a selected volume of the fluid chemical reagent 94 is dispensed into a well formed by the well openings 109 and 117, so that each one of the arc electrodes partially surrounds, and is in contact with, the fluid chemical reagent 94. The fluid chemical reagent 94 can be a biological reagent such as an electrolyte or an enzyme, for example, or another substance that is biologically configured to react with blood of an organism. Alternatively, the fluid chemical reagent 94 can be an environmental reagent such as a gaseous oxidizer, a liquid, a gel, or a paste that contains a gas. Such an environmental reagent can be, for example, an electrolyte that can sense continuously the presence of, or an amount of, carbon dioxide, carbon monoxide, or oxygen. A dispensing operation can be automated and precisely controlled so that a few microliters of the fluid chemical reagent 94 is delivered by a syringe at precisely the location of the well. The fabrication system is designed to be universal, regardless of the type or form of the fluid chemical reagent 94 in the active layer, or its end use.

Figure 4D:
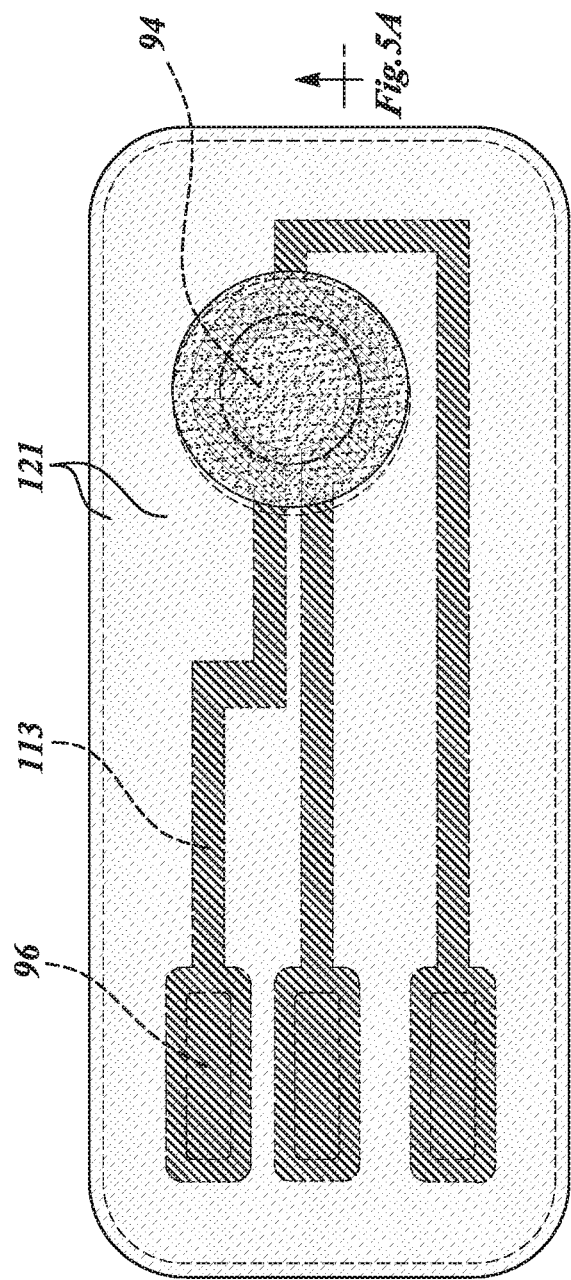
FIG. 4D is a top plan view of the micro-sensor after application of a peeling tape.

At 110, a peeling tape 121 is laminated onto the micro-sensors containing the fluid chemical reagent 94 to form the flexible backing 97, together with the first and second polymer layers, 103 and 115. FIG. 4D shows one embodiment of the partially fabricated fluid electrochemical micro-sensor following lamination of the peeling tape 121, which is shown herein as a translucent covering. The peeling tape 121 is placed over the rigid substrate 105 so as to cover all of the micro-sensors that contain the fluid chemical reagent 94. The peeling tape 121 can be made of a polymer film, such as polyimide or a dry photoresist, having a thickness of about 150 µm. The thickness of the peeling tape 121 can vary within the range of about 5-200 µm. In one embodiment, the peeling tape 121 is attached using a lamination process in which heat and pressure are applied directly to the peeling tape 121. The lamination process causes the peeling tape 121 to adhere to the micro-sensors, and temporarily to the substrate 105, while the peeling tape 121 can be removed with ease from the substrate 105 at a later time. Following lamination, the peeling tape 121 is cured, for example, by exposure to ultraviolet light at a low temperature that is compatible with the fluid chemical reagent 94.

As shown in FIG. 4D, the fluid chemical reagent 94 remains bounded on the bottom by the rigid substrate 105, while a top surface of the fluid chemical reagent 94 is held in place by the peeling tape 121. FIG. 4D can be compared directly with the cross-sectional view shown in FIG. 5A. It is noted that both the rigid substrate 105 and the peeling tape 121 are present in FIG. 5A, which illustrates a formed micro-sensor 90 sandwiched between the peeling tape 121 and the rigid substrate 105.

At 112, the laminated micro-sensors can be singulated, or cut, to yield individual micro-sensors, still attached to the substrate 105. One or more of the three mask patterns used in fabrication of the micro-sensors can include scribe lines to guide singulation. The singulation step can be executed using a laser beam.

Figure 5A:
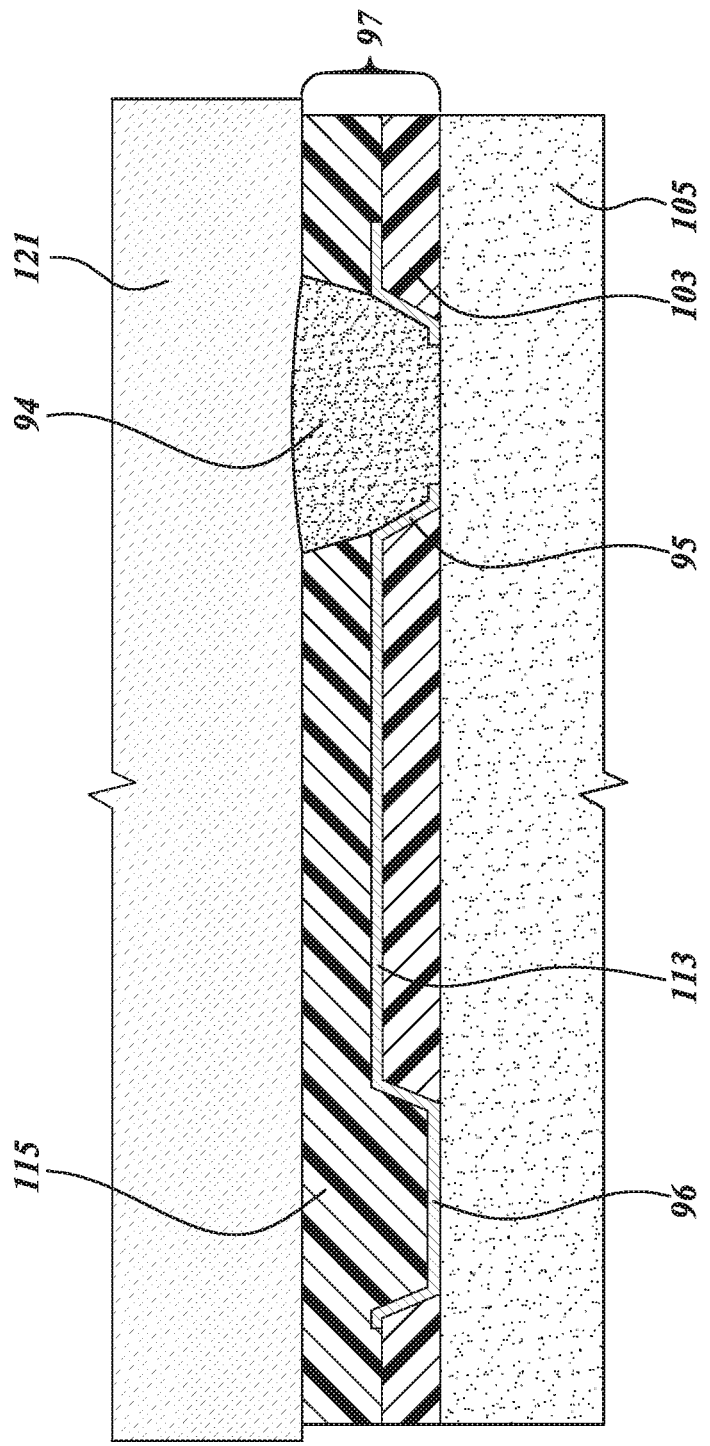
FIG. 5A is a cross-sectional view of the micro-sensor shown in FIG. 4D.

At 114, the individual micro-sensors are separated from the substrate 105 to produce the completed individual flexible electrochemical micro-sensors 90. After the method 100 is complete, the rigid substrate 105 is not retained as an element of the completed micro-sensors, which are designed to be flexible. FIGS. 5B and 5C illustrate one embodiment of a completed, flexible fluid electrochemical micro-sensor 90 following separation from the rigid substrate 105, wherein the peeling tape 121 now takes the place of the rigid substrate 105. Separation from the rigid substrate 105 occurs as the peeling tape 121 together with the microsensor are peeled off the rigid substrate 105 and inverted. The resulting individual flexible electrochemical micro-sensor 90 is shown in mirror image with the fluid chemical reagent 94 shown on the left, and right side up, in FIGS. 5B and 5C, following peeling, as opposed to the upside down view shown in FIG. 5A that shows the fluid chemical reagent 94 on the right. It is noted that in FIG. 5C, the contacts 96 are exposed at the surface of the micro-sensor 90.

Prior to step 114, the fluid chemical reagent 94 is surrounded by the rigid substrate 105 on one side, and the peeling tape 121 on the other side. The chemical reagent 94, for example, an electrolyte or enzyme, thus is protected against environmental degradation during processing because it is not exposed to the environment until it is separated from the substrate 105. This can be an important advantage of the current method over other methods in which the chemical reagent 94 is exposed to humidity and temperature fluctuations during processing. Because many chemical reagents 94 have relatively short lifespans, without such protection they could be degraded by extreme environmental conditions present during fabrication, before the product is completed or sold.

Figure 7A:
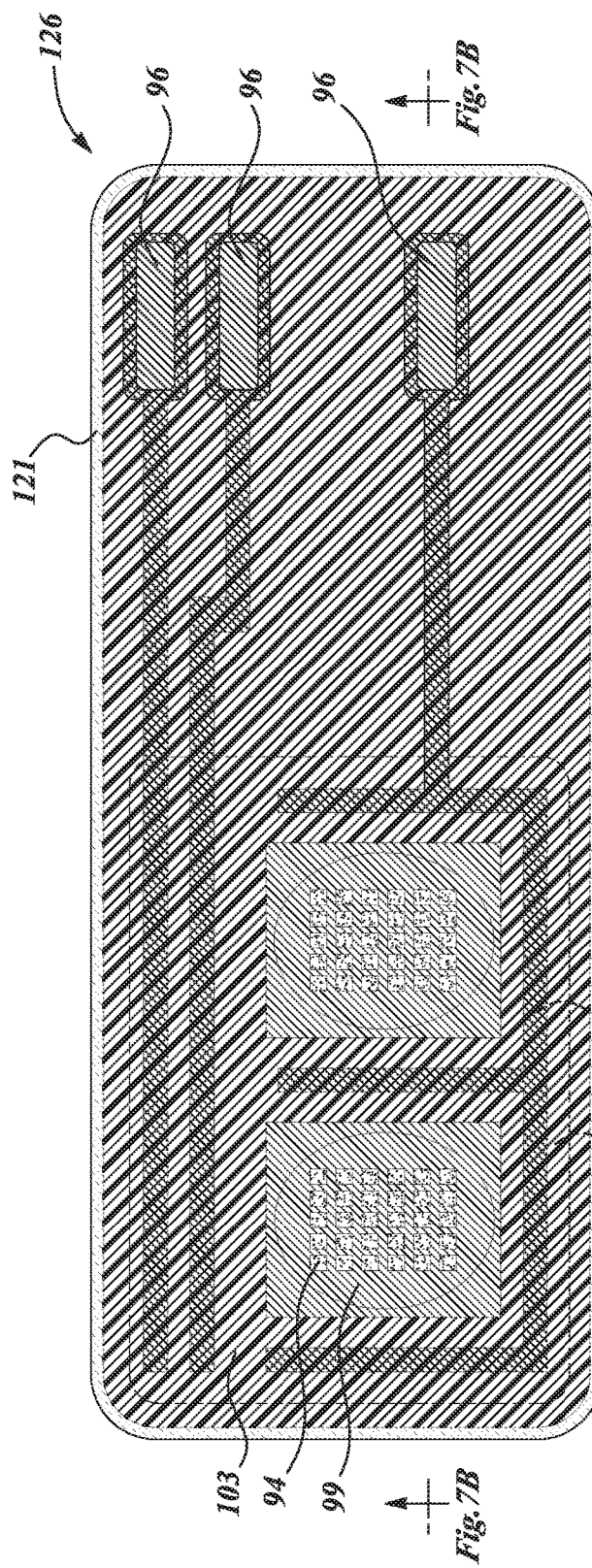
FIG. 7A is a top plan view of the completed universal micro-sensor dual reservoir embodiment shown in FIG. 6B, following separation from the glass carrier substrate.
Figure 7B:
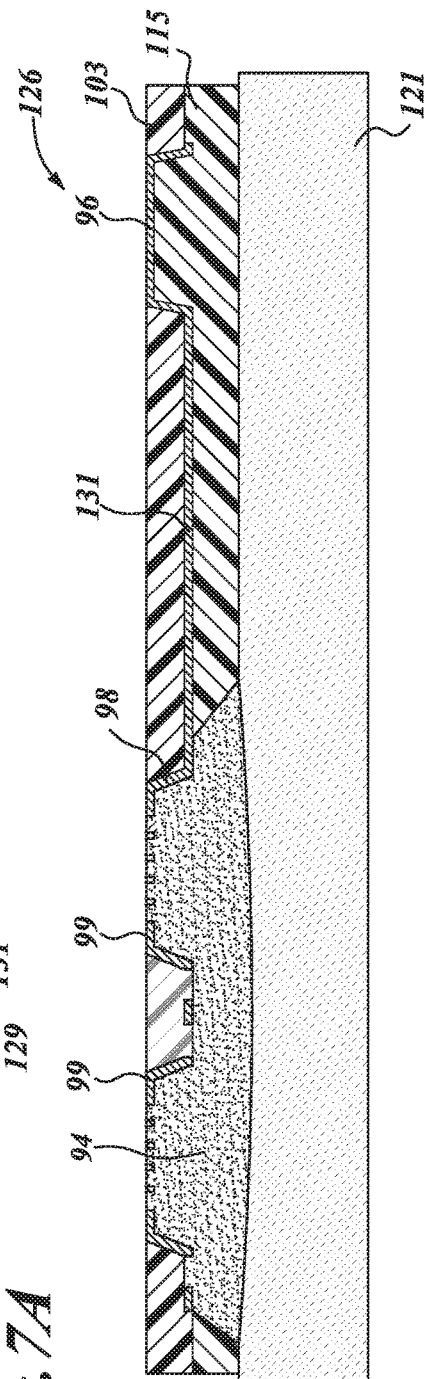
FIG. 7B is a cross-sectional view of the completed dual reservoir micro-sensor shown in FIG. 7A.

In the embodiments shown in FIGS. 5C and 7B, the final sensor strip has one side with the contacts 96 and the electrodes 95 exposed along with the reagent 94. This is the condition in which the sensor strip will be inserted into the electronic circuit for use. In some embodiments, this is the condition in which it shipped from the distributor to the customers. In other embodiments, a protective backing made of an easy to remove material is a placed overlying the electrodes 95 and the reagent 94 and is peeled away just prior to use by the end user. For example, a paper substrate with a small amount of adhesive, a layer of tape, a support layer like wax paper or the like may be placed overlying the entire side having the contacts 96 and reagent 94 thereon to keep them clean and protected until just moments before use. In one embodiment, the protective cover includes a layer that is electrically conductive, such as a thin layer of tin foil, aluminum foil or the like. In one embodiment, the conductive layer is in contact with all the contacts 96 and shorts all the electrodes together when the product is being stored and not yet in use. This ensures that no stray electrical charges can build up one electrode and that all electrodes are held at the same voltage. This keeps the reagent active and ready while protecting it from premature degradation. In a further embodiment, the conductive layer is separated from the electrodes 95 and/or contacts 96 by a thin insulating layer so that the conductive layer acts as an RF shield, an electrostatic discharge (ESD) shield, and provides other protection to ensure that the electrodes 96 and the reagent 94 are properly isolated from interaction with the outside chemical and electrical environment until ready for use.

Initiation of the peeling process from a glass carrier substrate for example, can be facilitated by submersing one end of the singulated micro-sensor in a water bath to separate the edge of the peeling tape 121 from the substrate 105. In FIG. 5C it is clearly shown that, after peeling, at least a portion of a surface 125 of the fluid chemical reagent 94 is exposed to the ambient environment. Thus, if the fluid chemical reagent 94 is a liquid, the micro-sensor must be removed from the water bath prior to exposing the fluid chemical reagent 94, or the fluid chemical reagent 94 may leak out and be lost. Consequently, the fluid chemical reagent 94 is preferably in the form of a gel or a paste, although the fluid chemical reagent 94 alternatively can be a liquid. During use of the micro-sensor as a biosensor, it is advantageous for the fluid chemical reagent 94 to be exposed to the ambient environment within an organism. Such exposure facilitates reacting the fluid chemical reagent 94 with bodily fluids of the organism, such as blood. During use as an environmental micro-sensor, it is also advantageous for the fluid electrochemical micro-sensor 90 to be exposed to the ambient environment to facilitate chemical reactions with the atmosphere.

Figure 6A:
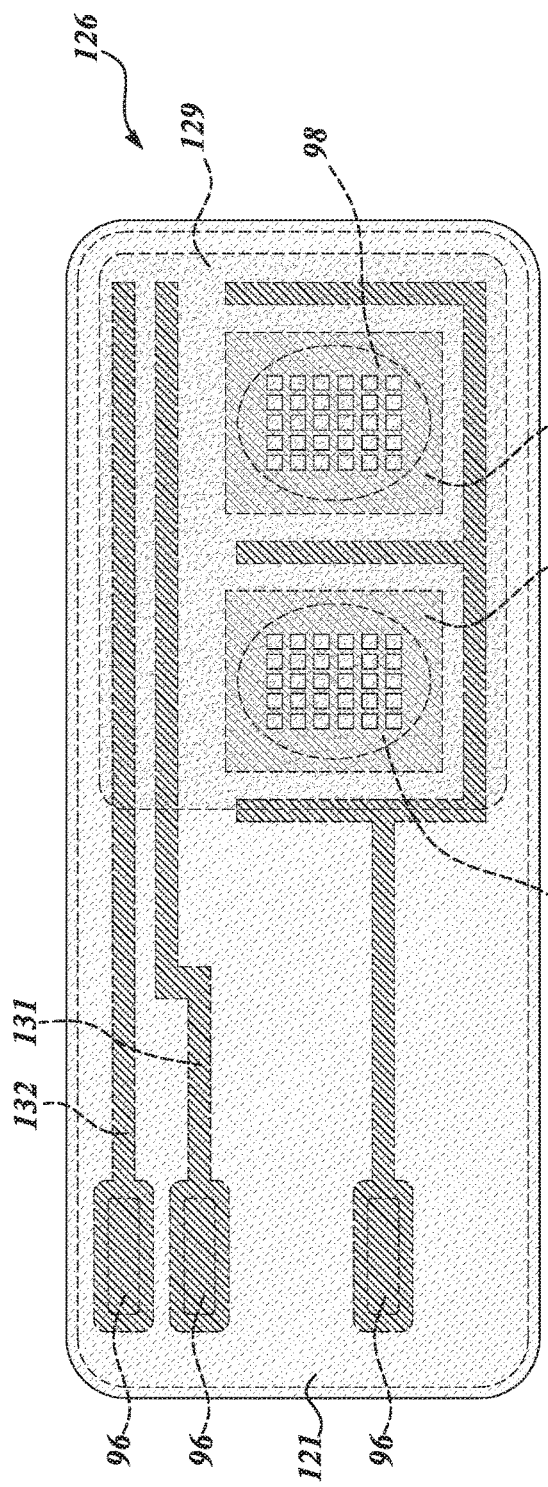
FIGS. 6A and 6B are top plan views of two alternative embodiments of the universal electrochemical fluid micro-sensor, shown after application of the peeling tape.
Figure 6B:
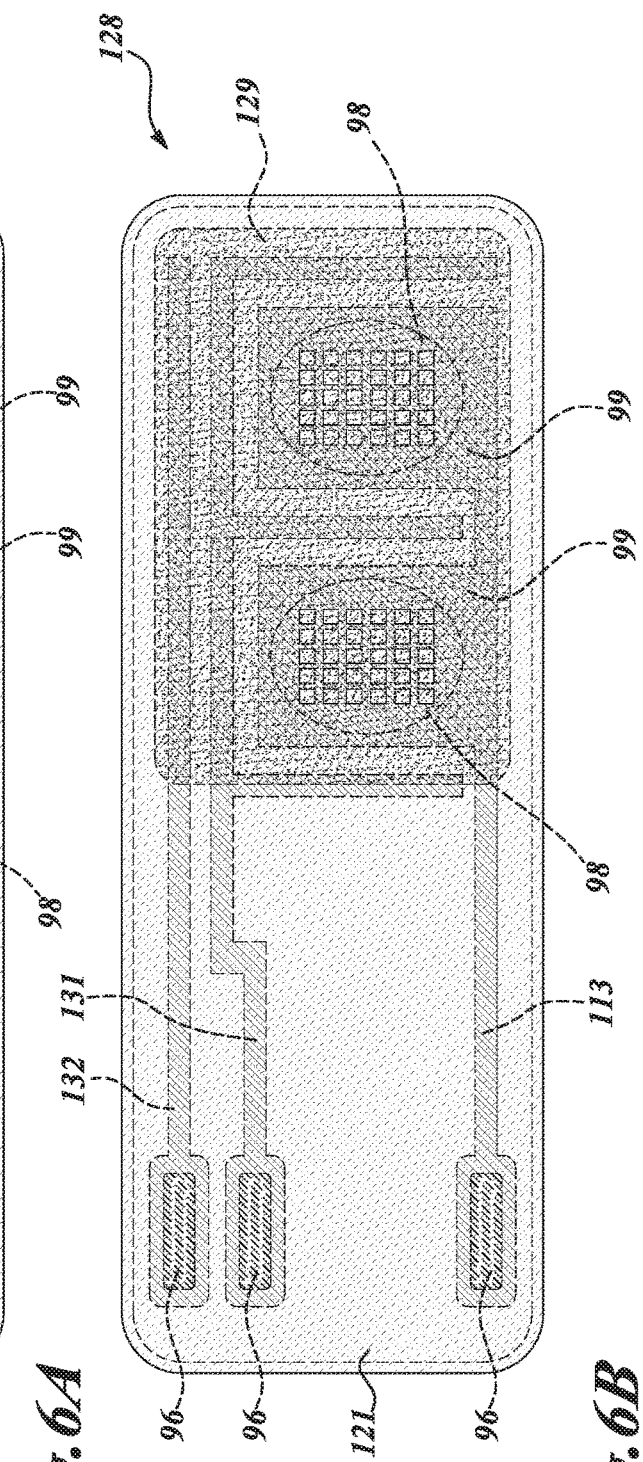

FIGS. 6A and 6B show top plan views of two alternative embodiments of the fluid electrochemical micro-sensor 90 following lamination of the peeling tape 121 at 110, but prior to separation from the rigid substrate 105 at 114. FIGS. 6A and 6B can be compared directly with the embodiment shown in FIG. 4D, which shows the fluid electrochemical micro-sensor 90, having a single circular reservoir 98 that contains the fluid chemical reagent 94 and exposes all of the surface area of the fluid. In contrast, embodiments of the micro-sensors 126 and 128 shown in FIGS. 6A and 6B, respectively, each include a large rectangular active area 129 in which fluid is contained by a pair of reservoirs 98 covered by species inlet nets 99. Each species inlet net 99 provides a confinement structure and a conduction path for the exposed portion of the surface of the fluid chemical reagent 94 following the peeling step at 114. The species inlet net 99 is desirably in the form of a conductive micromesh having dimensions selected in accordance with the viscosity of the fluid chemical reagent 94 such that a more viscous fluid chemical reagent 94 can be confined by a conductive micromesh having wider spacing. For example, a wider micromesh having openings about 100 microns wide may be sufficient to contain a fluid chemical reagent 94 in the form of a gel. Whereas, use of a less viscous fluid chemical reagent 94 may benefit from a finer mesh having smaller openings of about 10-20 microns.

While the traces 113 shown in FIG. 4D are coupled directly to the electrodes 95, the traces 131 shown in FIGS. 6A and 6B can be coupled capacitively or inductively to the species inlet nets 99 that are in contact with the electrolytic fluid chemical reagent 94. Signals can be transmitted via the contacts 96, or, in similar fashion to an RFID tag, the species inlet nets 99 and traces 131 can act as radiating antenna elements to communicate data wirelessly to an external receiver. FIGS. 6A and 6B show two different arrangements of the species inlet nets 99 and the traces 113 for use in capacitive or inductive coupling. The micro-sensor 126 shown in FIG. 6A includes three electrodes in addition to the species inlet nets 99. The micro-sensor 128 shown in FIG. 6B includes two electrodes in addition to the species inlet nets 99, which are directly coupled to the third electrode. A reference electrode 132 is also provided in each of the inductively coupled micro-sensors 126 and 128.

FIGS. 7A and 7B illustrate the micro-sensor embodiment 126 of FIG. 6A from a top plan view and a cross-sectional view, respectively, following completion of the fabrication process 100. Approximate dimensions of the finished fluid electrochemical micro-sensor are 5 mm×3 mm×0.2 mm. The thickness of each active area below the species inlet net is about 1 mm²×0.05 mm. The universal fluid electrochemical micro-sensor can be packaged in a canister to provide control of ambient humidity prior to its use, for up to 1-2 years.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
a substrate;
at least one insulating layer on the substrate, the at least one insulating layer having a first opening;
a first well extending through the at least one insulating layer, the first well aligned with the first opening; and
a first radiating antenna element that includes:
a first trace on the at least one insulating layer; and
a first species inlet net at the first opening, the first species inlet net is capacitively or inductively coupled to the first trace.

2. The device of claim 1 further comprising:
the at least one insulating layer having a second opening;
a second well extending through the at least one insulating layer, the second well aligned with the second opening; and
the first radiating antenna element further including:
a second species inlet net at the second opening, the second species inlet net coupled to the first trace.

3. The device of claim 2 wherein the first trace extends between the first well and the second well.

4. The device of claim 2 further comprising:
a second radiating antenna element that includes:
a second trace on the at least one polymer layer.

5. The device of claim 4 wherein the second trace extends between the first well and the second well.

6. The device of claim 2 further comprising:
a reagent contained in the first well and the second well, the first species inlet net at least partially covering the first opening and the second species inlet net at least partially covering the second opening.

7. The device of claim 1 further comprising:
a second radiating antenna element that includes:
a second trace on the at least one insulating layer.

8. The device of claim 1 further comprising:
a reagent contained in the first well, the first species inlet net at least partially covering the first opening.

9. A device, comprising:
a substrate;
a first polymer layer on the substrate;
a second polymer layer on the first polymer layer;
a first well extending through the first and second polymer layers;
a second well extending through the first and second polymer layers;
a plurality of traces at least partially embedded between the first polymer layer and the second polymer layer; and
a first radiating antenna element to wirelessly communicate data to an external receiver, the first radiating antenna element including:
a first species inlet net at the first well; and
a second species inlet net at the second well.

10. The device of claim 9 wherein the first radiating antenna element further includes:
one of the plurality of traces directly coupled to the first species inlet net and the second species inlet net.

11. The device of claim 10 wherein a second one of the plurality of the plurality of traces extends between the first well and the second well.

12. The device of claim 9 wherein the first radiating antenna element further includes:
a first one of the plurality of traces capacitively or inductively coupled to the first species inlet net and the second species inlet net.

13. The device of claim 12 further comprising:
a second radiating antenna element to wirelessly communicate data to the external receiver, the second radiating antenna element including a second one of the plurality of traces.

14. The device of claim 9 further comprising:
a second radiating antenna element to wirelessly communicate data to the external receiver, the second radiating antenna element including one of the plurality of traces.

15. A device, comprising:
a substrate;
an insulating layer on the substrate;
a well extending through the insulating layer;
a contact on the insulating layer;
an electrode extending along a portion of the well; and
an antenna to wirelessly communicate data to an external receiver that includes:
a trace coupled between the electrode and the contact.

16. The device of claim 15 further comprising:
a fluid in the well, the electrode being in contact with the fluid.

17. The device of claim 15 wherein the insulating layer further includes an opening aligned with the well, the electrode extending over at least a portion of the opening.

18. The device of claim 15 wherein the antenna further includes the electrode.

19. The device of claim 15 wherein the trace is at least partially embedded in the insulating layer.

20. The device of claim 19 wherein the insulating layer includes a first insulating layer on the substrate and a second insulating layer on the first insulating layer, the trace at least partially embedded between the first insulating layer and the second insulating layer.

* * * * *